United States Patent
Furuya et al.

(10) Patent No.: US 9,206,119 B2
(45) Date of Patent: Dec. 8, 2015

(54) PROCESS FOR PREPARING β-MERCAPTOCARBOXYLIC ACID

(71) Applicant: Mitsui Chemicals, Inc., Minato-ku (JP)

(72) Inventors: Masayuki Furuya, Arao (JP); Tatsuya Ogawa, Ravenna (IT); Takeshi Nishimura, Yanagawa (JP)

(73) Assignee: MITSUI CHEMICALS INC., Tokyo (JP)

( * ) Notice: Subject to any disclaimer, the term of this patent is extended or adjusted under 35 U.S.C. 154(b) by 0 days.

(21) Appl. No.: 14/359,407

(22) PCT Filed: Nov. 20, 2012

(86) PCT No.: PCT/JP2012/007451
§ 371 (c)(1),
(2) Date: May 20, 2014

(87) PCT Pub. No.: WO2013/076968
PCT Pub. Date: May 30, 2013

(65) Prior Publication Data
US 2014/0288329 A1 Sep. 25, 2014

(30) Foreign Application Priority Data
Nov. 21, 2011 (JP) .................................. 2011-253453

(51) Int. Cl.
*C07C 319/04* (2006.01)
*C07C 319/28* (2006.01)

(52) U.S. Cl.
CPC ............. *C07C 319/04* (2013.01); *C07C 319/28* (2013.01)

(58) Field of Classification Search
CPC ............................ C07C 319/28; C07C 319/04
See application file for complete search history.

(56) References Cited

U.S. PATENT DOCUMENTS

| | | | |
|---|---|---|---|
| 3,948,816 A | 4/1976 | Helmlinger et al. | |
| 4,067,901 A | 1/1978 | Gladstone et al. | |
| 5,157,147 A | 10/1992 | Chisholm et al. | |
| 5,256,818 A | 10/1993 | Tomioka | |
| 6,689,907 B1 * | 2/2004 | Labat ............................ | 562/512 |

FOREIGN PATENT DOCUMENTS

| | | | |
|---|---|---|---|
| GB | 1336037 A | 11/1973 | |
| JP | 40-15170 B1 | 7/1965 | |
| JP | 47-12317 A | 6/1972 | |
| JP | 52-36623 A | 3/1977 | |
| JP | 58-54138 B2 | 12/1983 | |
| JP | 59-29655 | 2/1984 | |
| JP | 61-254555 A | 11/1986 | |
| JP | 2-121962 A | 5/1990 | |
| JP | 4-9363 A | 1/1992 | |
| JP | 4-273851 A | 9/1992 | |
| JP | 9-249639 | 9/1997 | |
| JP | 10-95760 | 4/1998 | |
| JP | 2000-501723 A | 2/2000 | |
| JP | 2001-187778 A | 7/2001 | |
| WO | WO 2010/095745 A1 | 8/2010 | |

OTHER PUBLICATIONS

Office Action issued in corresponding Japanese application on Sep. 24, 2014 (2 pages).
Office Action issued in corresponding Chinese application on Jan. 4, 2015 (5 pages).
Office Action issued in corresponding Japanese application on Jan. 20, 2015 (3 pages).
International Search Report (PCT/ISA/210) mailed on Feb. 26, 2013, by the Japanese Patent Office as the International Searching Authority for International Application No. PCT/JP2012/007452.
International Search Report (PCT/ISA/210) mailed on Feb. 26, 2013, by the Japanese Patent Office as the International Searching Authority for International Application No. PCT/JP2012/007451.

* cited by examiner

*Primary Examiner* — Yong Chu
(74) *Attorney, Agent, or Firm* — Buchanan, Ingersoll & Rooney

(57) ABSTRACT

There is provided a process for preparing β-mercaptocarboxylic acid represented by the following General Formula (3) comprising step of reacting hydrogen sulfide, alkali hydroxide represented by a formula: XOH (X represents Na or K), and unsaturated carboxylic acid represented by the following General Formula (1) under atmospheric pressure to obtain a reaction solution including a compound represented by the following General Formula (2) and step of neutralizing the reaction solution in an acid. An amount of the alkali hydroxide is equal to or greater than total moles of the unsaturated carboxylic acid and the hydrogen sulfide.

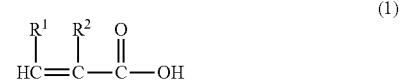

(1)

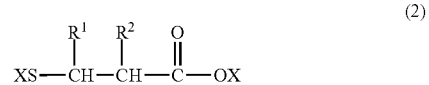

(2)

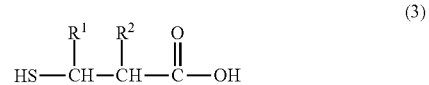

(3)

4 Claims, No Drawings

PROCESS FOR PREPARING β-MERCAPTOCARBOXYLIC ACID

TECHNICAL FIELD

The present invention relates to a process for preparing β-mercaptocarboxylic acid using unsaturated carboxylic acid.

BACKGROUND ART

β-mercaptocarboxylic acid is a compound which is useful as a raw material for organic synthesis products including agricultural chemicals, and pharmaceuticals, and is useful as a raw material for a stabilizer of vinyl chloride, a cross-linking agent of an epoxy resin and an acrylic acid ester polymer, and a plastic lens monomer.

Examples of the process for preparing β-mercaptocarboxylic acid are as follows.

Patent Document 1 discloses a method in which acrylic acid and thiosulfate are reacted in an aqueous medium, as a result to produce Bunte salt as a precursor of β-mercaptopropionic acid, and then, the Bunte salt is hydrolyzed in the presence of an acid.

Patent Document 2 discloses a method in which an acrylic acid alkali salt aqueous solution is added to an aqueous solution of alkali hydrosulfide to react in the presence of an alkali hydroxide, the resultant is neutralized with an acid, and a reduction treatment is performed thereto with zinc.

Patent Document 3 discloses a method in which, in a method in which unsaturated carboxylic acid and a hydrogen sulfide compound are reacted, the obtained reaction medium is acidified to produce mercaptocarboxylic acid, hydrogen sulfide other than hydrogen sulfide provided in the neutralization of the unsaturated carboxylic acid is supplied, and the reaction is performed under the pressurization of at least 8 bar. In addition, Patent Document 3 discloses that a hydrogen sulfide compound is obtained by the reaction of $H_2S$ and sodium hydroxide.

Patent Document 4 discloses a method in which β-unsaturated carboxylic acid and hydrogen sulfide are reacted in an aqueous solution in the presence of a basic compound to produce β-mercaptocarboxylic acid, and the above-described reaction is performed under pressure conditions of 3.5 MPaG to 20.0 MPaG.

Patent Document 5 discloses a method in which when unsaturated nitrile is added to an aqueous solution of alkali hydrosulfide to react, the resultant is neutralized, and is hydrolyzed to prepare mercaptocarboxylic acid, sulfur is used.

RELATED DOCUMENT

Patent Document

[Patent Document 1] Japanese Unexamined Patent Publication No. S59-29655
[Patent Document 2] Japanese Unexamined Patent Publication No. 2001-187778
[Patent Document 3] PCT Japanese Translation Patent Publication No. 2000-501723
[Patent Document 4] Pamphlet of International Publication No. WO2010/095745
[Patent Document 5] Japanese Unexamined Patent Publication No. H2-121962

DISCLOSURE OF THE INVENTION

The techniques of the patent documents described above have the following problems.

In the reaction in Patent document 2, it is necessary to use alkali hydrosulfide as a raw material. However, since dithiodicarboxylic acid is largely produced as a by-product, the reaction yield was decreased. In addition, it is possible to obtain β-mercaptocarboxylic acid by reduction of the dithiodicarboxylic acid. However, since the used amount of a reducing agent becomes large, manufacturing cost is increased, and there was a problem in that waste is increased after the reaction. Moreover, as described in paragraph [0007], the method in the documents is characterized in that hydrogen sulfide is not used.

In Patent Document 3 or 4, since the reaction was performed under the pressurization, and it was necessary to maintain a pressurized state, the manufacturing process was complicated. In addition, it is necessary to separately provide manufacturing equipment for pressurization and pressure-resistant apparatus, and burden of manufacturing cost is increased. Moreover, in the comparative example 1 in Patent document 4 describes that the reaction is performed at atmospheric pressure. However, there was room for improving the reaction yield.

The present invention has been made to solve the above-described problems, and can be described as follows.

[1] A process for preparing β-mercaptocarboxylic acid represented by the following General Formula (3) comprising: reacting hydrogen sulfide, alkali hydroxide represented by a formula: XOH (X represents Na or K), and unsaturated carboxylic acid represented by the following General Formula (1) under atmospheric pressure to obtain a reaction solution including a compound represented by the following General Formula (2), and neutralizing the reaction solution in an acid, in which the amount of the alkali hydroxide is equal to or greater than the total moles of the unsaturated carboxylic acid and the hydrogen sulfide.

(In Formula (1), each of $R^1$ and $R^2$ independently represents hydrogen or an alkyl group of C1 to C4, and may be the same as or different from each other.)

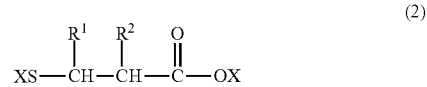

(In Formula (2), $R^1$ and $R^2$ have the same definition as in Formula (1), X has the same definition as in alkali hydroxide represented by a formula: XOH.)

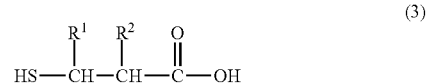

(In Formula (3), $R^1$ and $R^2$ have the same definition as in Formula (1).)

[2] The process for preparing β-mercaptocarboxylic acid described in [1], in which the step for obtaining the reaction solution is performed in the presence of sulfur.

[3] The process for preparing β-mercaptocarboxylic acid described in [1] or [2], in which the step of neutralizing the reaction solution in an acid includes a step in which dithiodicarboxylic acid produced from β-mercaptocarboxylic acid is reduced by a metal.

The "under atmospheric pressure" includes a fine pressurization state generated at the time of blowing hydrogen sulfide, and is in the range of about 0.09 MPa to 0.13 MPa.

According to the present invention, it is possible to obtain mercaptocarboxylic acid with high yield under atmospheric pressure. In addition, it is possible to suppress the production of dithiodicarboxylic acid as a by-product at the time of neutralizing the reaction solution using hydrogen sulfide as a raw material, and it is possible to provide a simplified method industrially.

DESCRIPTION OF EMBODIMENTS

Hereinafter, the invention will be described.
The process for preparing β-mercaptocarboxylic acid of the present invention has the following Steps a and b.
Each step will be described in order.
[Step a]
Hydrogen sulfide, alkali hydroxide represented by a formula: XOH (X represents Na or K) and unsaturated carboxylic acid represented by the following General Formula (1) are reacted under atmospheric pressure, whereby a reaction solution containing the compound represented by the following General Formula (2) is obtained.

(1)

In Formula (1), each of $R^1$ and $R^2$ independently represents hydrogen or an alkyl group of C1 to C4, and may be the same as or different from each other.

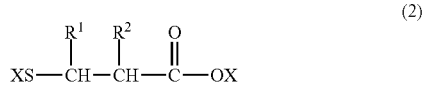
(2)

In Formula (2), $R^1$ and $R^2$ have the same definition as in Formula (1), X has the same definition as in alkali hydroxide represented by a formula: XOH.

In Step a, the amount of the alkali hydroxide is equal to or greater than the total moles of the unsaturated carboxylic acid represented by General Formula (1) and the hydrogen sulfide. Thus, it is also possible to obtain mercaptocarboxylic acid with high yield under atmospheric pressure.

Moreover, the amount of the alkali hydroxide is preferably equal to or greater than 1 time, more preferably equal to or greater than 1.5 times with respect to the total moles of the unsaturated carboxylic acid and the hydrogen sulfide. After the reaction is completed, if the amount of acid for neutralizing the reaction solution is increased, the upper limit value affects an increase in cost. From the viewpoint of this, the upper limit value is equal to or less than 5 times, preferably equal to or less than 4 times, and more preferably equal to or less than 2.5 times. These upper limit values and lower limit values can be arbitrarily combined.

In the present invention, Step a can be performed by a method described below.

(1) Unsaturated carboxylic acid represented by General Formula (1) is added to an aqueous solution of alkali hydroxide to produce a salt is formed. Next, hydrogen sulfide is blown to react with unsaturated carboxylic acid salt.

(2) Hydrogen sulfide is blown into an aqueous solution of alkali hydroxide, and then, unsaturated carboxylic acid represented by General Formula (1) is added thereto, whereby reaction occurs.

Moreover, in the methods (1) and (2), the example in which unsaturated carboxylic acid is added is described. However, alkali salt of unsaturated carboxylic acid which is prepared in advance using an alkali hydroxide may be used. In this case, Step a can be performed by a method (3) described below.

(3) Hydrogen sulfide is blown into an aqueous solution of alkali hydroxide, and then, aqueous solution containing alkali salt of unsaturated carboxylic acid which is separately prepared by adding unsaturated carboxylic acid to the aqueous solution of alkali hydroxide is added thereto, whereby reaction occurs.

Moreover, in the case of the method (3), the amount of the alkali hydroxide includes an amount of the alkali hydroxide used to produce the alkali salt of unsaturated carboxylic acid in advance.

In Step a, as the unsaturated carboxylic acid of General Formula (1) in which preferably, each of $R^1$ and $R^2$ independently represents hydrogen or a methyl group, specifically, acrylic acid, methacrylic acid and crotonic acid can be exemplified. In the case where β-mercaptopropionic acid used in a plastic lens monomer is prepared, acrylic acid can be used.

Alkali hydroxide is represented by a formula: XOH (X represents Na or K), and X is preferably sodium. Alkali hydroxide is used as an aqueous solution as described in the above-described method. Alkali hydroxide may be dissolved in a mixed solvent of water and alcohol, and alcohol may be separately added thereto. Since a solvent recovery step is not needed, the above method is advantageous from the viewpoint of productivity improvement compared to methods using an organic solvent in the related art.

As hydrogen sulfide, hydrogen sulfide which is derived from petroleum refining, and hydrogen sulfide which is synthesized by hydrogenation of sulfur can be exemplified. In Step a, in the case where hydrogen sulfide is supplied to an aqueous solution of alkali hydroxide, hydrogen sulfide gas is used. However, liquefied hydrogen sulfide is usually used since storage stability thereof is excellent.

The added amount of hydrogen sulfide is preferably equal to or greater than 1.0 equivalent weight, and more preferably equal to or greater than 1.5 equivalent with respect to the unsaturated carboxylic acid. The upper limit value is equal to or less than 9.0 equivalent, preferably equal to or less than 5.0 equivalent, and more preferably equal to or less than 3.0 equivalent. These upper limit value and lower limit value can be arbitrarily combined.

A hydrogen sulfide gas can be supplied to the aqueous solution of alkali hydroxide while a temperature of the aqueous solution is maintained at the range of 0° C. to 50° C. Thus, solubility of hydrogen sulfide gas is improved, and the reaction rapidly proceeds. After hydrogen sulfide gas is supplied, the reaction is usually performed in the temperature range of 20° C. to 150° C., preferably in the temperature range of 50° C. to 140° C., and more preferably in the temperature range of 80° C. to 130° C. The temperature range is preferable from the viewpoint of a reaction rate and of reducing the production amount of by-products (dithiodicarboxylic acid and thiodicarboxylic acid). The reaction time can be suitably selected depending on the reaction temperature. The reaction time is usually in the range of 0.5 hours to 20 hours, preferably in the range of 1 hour to 15 hours, more preferably in the range of 2 hours to 10 hours, and still more preferably in the range of 3 hours to 10 hours.

In addition, in Step a, the reaction can be performed in the presence of sulfur in order to promote the reaction. Thus, the reaction of mercaptocarboxylic acid can be completed in a shorter time.

The added amount of sulfur is in the range of 0.01 mol % to 10 mol %, preferably in the range of 0.1 mol % to 5 mol %, and more preferably in the range of 0.1 mol % to 3 mol % with respect to the unsaturated carboxylic acid from the viewpoint of the above-described effect. The addition method is not particularly limited, and at the time of adding unsaturated carboxylic acid or alkali salt of unsaturated carboxylic acid, these are preferably present in aqueous solution.

According to Step a, reaction solution including the compound represented by General Formula (2) can be obtained. The reaction solution includes thiodicarboxylic acid in addition to this compound.

[Step b]

The reaction solution obtained in Step a is neutralized with an acid to produce β-mercaptocarboxylic acid represented by the following General Formula (3) from the compound represented by General Formula (2).

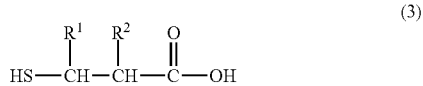

(3)

In Formula (3), $R^1$ and $R^2$ have the same definition as in Formula (1).

As an acid, mineral acids such as sulfuric acid, hydrochloric acid, nitric acid and phosphoric acid, and lower carboxylic acids such as formic acid, and acetic acid can be used.

The acid is used in an amount that the reaction system exhibits acidity, and usually, the range of 0.8 equivalents to 1.2 equivalents is suitable with respect to alkali hydroxide which is used in the reaction. At the time of adding, it is preferably performed while checking a pH of the reaction solution with a pH meter, and pH is set to be in the range of 1 to 3.

According to Step a, a reaction solution including β-mercaptocarboxylic acid represented by General Formula (3) and thiodicarboxylic acid can be obtained. In addition to these compounds, the reaction solution contains dithiodicarboxylic acid which is produced from β-mercaptocarboxylic acid and the like.

[Reduction Step]

In the present invention, a step in which produced dithiodicarboxylic acid is reduced by a metal is included from the viewpoint of improving the yield of β-mercaptocarboxylic acid. Moreover, the reduction step can be performed after Step b (neutralizing step) or simultaneously with Step b.

In the reducing step, β-mercaptocarboxylic acid which is a target substance is not immediately obtained from the reaction mixture after neutralization. A reducing agent is added to the solution after the reaction is completed, or the reaction solution obtained by the neutralization, and a reduction reaction is performed under acidic conditions. Thus, dithiodicarboxylic acid which is a by-product can be converted to β-mercaptocarboxylic acid, and the improvement of the yield can be achieved.

A metal which is a reducing agent includes zinc, iron and tin and the like. Among these, iron is preferably used from the viewpoint of economic efficiency and reduction of the burden on the environment. Moreover, these reducing agents may used singly or in a combination of two or more kinds thereof. The used amount of the reducing agent is preferably in the range of 1.0 mole to 5 moles, and more preferably in the range of 1.2 moles to 3 moles with respect to 1 mole of dithiodicarboxylic acid which is obtained as a by-product from the viewpoint of improving the yield and economic efficiency.

In the process for preparing of the present invention, the production amount of dithiodicarboxylic acid is small compared to a method in which the NaSH is added, and therefore, the reaction yield of β-mercaptocarboxylic acid can be improved. In addition, since the production amount of dithiodicarboxylic acid is small, the amount of waste derived from metals used in the reduction can be reduced.

Since β-mercaptocarboxylic acid is dissolved in an aqueous layer obtained after the neutralization, it is extracted from the aqueous layer by an organic solvent. The organic solvent includes ethyl acetate, butyl acetate, chloroform, dichloromethane, diethyl ether, isopropyl ether, methyl ethyl ketone and isobutyl ketone and the like, and it is preferably used ethyl acetate and butyl acetate.

After the extraction, the organic solvents are removed by concentration under reduced pressure or atmospheric pressure, and mercaptocarboxylic acid which is a target substance can be obtained by performing a distillation refinement. Moreover, the aqueous solution obtained after the extraction is an aqueous solution of inorganic salts such as high concentration sodium sulfate or sodium chloride, and for example, an aqueous solution of high purity sodium sulfate can be used. In addition, if crystals are precipitated from high concentration sodium sulfate solution, the precipitated crystals can be used as extremely high purity sodium sulfate. Furthermore, since organic substance and nitrogen compounds are rarely contained in the waste liquid, there is no the influence on the environment, pollution treatment is also very simple and economical.

In the case of being purified by distillation, distillation apparatus used for distillation is not particularly limited, and known distillation apparatus such as a batch type distillation apparatus, a continuous distillation apparatus and a tower type distillation apparatus can be used. In the case where industrially distilling a large amount, the continuous distillation apparatus composed of a heater, a rectifier and a condenser is preferably used from the viewpoint of stabilization of quality and productivity improvement.

In addition, after distillation, thiodicarboxylic acid which is a by-product is included in the residue. The distillation residue can be returned to Step a again (recycling step). Thiodicarboxylic acid which is included in the distillation residue can be used as a raw material of β-mercaptocarboxylic acid. At this time, from the viewpoint of fluidity of the distillation residue, after the temperature was increased to give fluidity thereto, or the distillation residue was diluted with a solvent, the distillation residue was returned to the reaction step, and it can be provided to the reaction. In addition, in the distillation step, without distilling off the total amount of the β-mercaptocarboxylic acid, distillation ending at a state in which β-mercaptocarboxylic acid was in the range of 5% to 50%, and preferably in the range of 10% to 30% in the distillation residue, it was returned to the reaction step as a β-mercaptocarboxylic acid solution of thiodicarboxylic acid, and it can also be provided to the reaction.

By repeatedly performing the step, a final yield of β-mercaptocarboxylic acid can be improved.

The present invention has been described above, and other configuration can be also employed within a range not interfering with the effect of the present invention.

EXAMPLES

Hereinafter, the present invention will be further described in more detail with Examples, and the scope of the present invention is not limited to Examples.

Example 1

A 5-necked flask provided with a stirring apparatus, a thermometer, a cooling tube, a dropping funnel and a blowing tube was prepared, 36.3 g (0.88 moles) of 97% sodium hydroxide and 43.3 g of water were introduced thereto, and the resultant was stirred until it became uniform. While maintaining the inner temperature of the flask at the range of 45° C. to 50° C. by heating the flask in an oil bath, 14.4 g (0.20 moles) of acrylic acid was added dropwise from the dropping funnel over 0.5 hours.

After the dropping ended, 12.6 g (0.37 moles) of hydrogen sulfide gas was blown into the reaction solution through the flow meter from a liquefied hydrogen sulfide bombe (manufactured by Sumitomo Seika Chemicals Co., Ltd.) at the same temperature over 88 minutes. After the blowing ended, the temperature was raised to 100° C., and reaction was performed at the same temperature over 8 hours. Moreover, when quantitative analysis of the reaction solution was performed by a HPLC after five hours of the reaction initiation, 76.1 mol % of β-mercaptopropionic acid sodium salt, 23.1 mol % of thiodipropionic acid sodium salt and 0.3 mol % of dithiodipropionic acid sodium salt as a by-product were produced.

After the reaction ended, as a result of quantitative analysis of the reaction solution, 86 mol % of β-mercaptopropionic acid sodium salt, and 13 mol % of thiodipropionic acid sodium salt and 0.4 mol % of dithiodipropionic acid sodium salt as a by-product were produced.

While bubbling nitrogen gas into the reaction system, 129.5 g (0.462 moles) of 35% aqueous sulfuric acid was added dropwise over 2.5 hours to neutralize the reaction solution. Hydrogen sulfide generated at this time was discharged from the upper portion of the cooling tube out of the system. In addition, in the reaction mass composition after the neutralization, β-mercaptopropionic acid was 86 mol %, and thiodipropionic acid and dithiodipropionic acid which are by-products were 13 mol % and 0.3 mol %, respectively.

After the degassing ended, 18.0 g of butyl acetate was introduced thereto, and an extraction operation was performed. 18.0 g of butyl acetate is further introduced to the aqueous layer obtained by a separation, and the same extraction operation was performed three times.

After the butyl acetate layers obtained by the extraction of three times were combined into one, butyl acetate was removed under reduced pressure using an evaporator. The obtained concentrated liquid was introduced into a kettle of a distillation apparatus with a single pipe, and distillation was performed under a reduced pressure of 1.2 KPa. Distillation ended when the kettle temperature is increased up to 150° C. The residue in the kettle had fluidity even at 100° C. As the main fraction, 17.5 g (0.165 moles) of β-mercaptopropionic acid having a purity of 99.9% was obtained. The yield with respect to acrylic acid was 82.5%.

Example 2

A 5-necked flask provided with a stirring apparatus, a thermometer, a cooling tube, a dropping funnel and a blowing tube was prepared, 36.3 g (0.88 moles) of 97% sodium hydroxide and 43.3 g of water were introduced thereto, and the resultant was stirred until it became uniform. While maintaining the inner temperature of the flask at the range of 45° C. to 50° C. by heating the flask in an oil bath, 14.4 g (0.20 moles) of acrylic acid was added dropwise from the dropping funnel over 0.5 hours.

After the dropping ended, 12.6 g (0.37 moles) of hydrogen sulfide gas was blown into the reaction solution through the flow meter from a liquefied hydrogen sulfide bombe (manufactured by Sumitomo Seika Chemicals Co., Ltd.) at the same temperature over 88 minutes. After the blowing ended, the temperature was raised to 100° C., and reaction was performed at the same temperature over 8 hours.

After the reaction ended, when quantitative analysis of the reaction solution was performed by a HPLC, 86.1 mol % of β-mercaptopropionic acid sodium salt, and 12.9 mol % of thiodipropionic acid sodium salt and 0.4 mol % of dithiodipropionic acid sodium salt as a by-product were produced.

After 0.04 g (0.0007 moles) of Fe powder was introduced into the reaction system, while bubbling nitrogen gas thereinto, 129.5 g (0.462 moles) of 35% aqueous sulfuric acid was added dropwise over 2.5 hours to reduce and to neutralize the reaction solution. Hydrogen sulfide generated at this time was discharged from the upper portion of the cooling tube out of the system. In the reaction mass composition after the neutralization, β-mercaptopropionic acid was 86.5 mol %, thiodipropionic acid which is a by-product was 12.9 moles, and dithiodipropionic acid was not detected.

Example 3

A 5-necked flask provided with a stirring apparatus, a thermometer, a cooling tube, a dropping funnel and a blowing tube was prepared, 36.3 g (0.88 moles) of 97% sodium hydroxide and 43.3 g of water and 0.072 g (0.0022 moles) of sulfur were introduced thereto, and the resultant was stirred until it became uniform.

While maintaining the inner temperature of the flask at the range of 45° C. to 50° C. by heating the flask in an oil bath, 14.4 g (0.20 moles) of acrylic acid was added dropwise from the dropping funnel over about 0.5 hours.

After the dropping ended, 12.6 g (0.37 moles) of hydrogen sulfide gas was blown into the reaction solution through the flow meter from a liquefied hydrogen sulfide bombe (manufactured by Sumitomo Seika Chemicals Co., Ltd.) at the same temperature over 88 minutes. After the blowing ended, the temperature was raised to 100° C., and reaction was initiated. When the reaction was conducted while performing a lap analysis of the reaction mass, 84.0 mol % of β-mercaptopropionic acid sodium salt, and 14.9 mol % of thiodipropionic acid sodium salt, 0.5 mol % of dithiodipropionic acid sodium salt as a by-product were produced after two hours of reaction initiation.

When the reaction ended after five hours of reaction initiation, 87.4 mol % of β-mercaptopropionic acid sodium salt, and 11.8 mol % of thiodipropionic acid sodium salt and 0.8 mol % of dithiodipropionic acid sodium salt as a by-product were produced.

Example 4

A 5-necked flask provided with a stirring apparatus, a thermometer, a cooling tube, a dropping funnel and a blowing tube was prepared, 47.0 g (1.14 moles) of 97% sodium hydroxide, 54.5 g of water and 0.072 g (0.0022 moles) of sulfur were introduced thereto, and the resultant was stirred until it became uniform.

While maintaining the inner temperature of the flask at the range of 45° C. to 50° C. by heating the flask in an oil bath, 14.4 g (0.20 moles) of acrylic acid was added dropwise from the dropping funnel over 0.5 hours.

After the dropping ended, 17.7 g (0.52 moles) of hydrogen sulfide gas was blown into the reaction solution through the flow meter from a liquefied hydrogen sulfide bombe (manufactured by Sumitomo Seika Chemicals Co., Ltd.) at the same temperature over 90 minutes. After the blowing ended, the temperature was raised to 100° C., and reaction was performed at the same temperature over 8 hours.

After the reaction ended, when quantitative analysis of the reaction solution was performed by a HPLC, 94.8 mol % of β-mercaptopropionic acid sodium salt, and 4.6 mol % of thiodipropionic acid sodium salt and 0.2 mol % of dithiodipropionic acid sodium salt as a by-product were produced.

Example 5

An operation was performed in the same manner as Example 1, and 17.5 g (0.165 moles) of β-mercaptopropionic acid having a purity of 99.9% as a main fraction, 2.8 g (15.7% by weight (0.004 moles) of β-mercaptopropionic acid, 81.5% by weight (0.012 moles) of thiodipropionic acid, and 2.3% by weight (0.0003 moles) of dithiodipropionic acid) as a residue (distillation residue (A)) of distillation kettle were obtained (Reaction 1).

A 5-necked flask provided with a stirring apparatus, a thermometer, a cooling tube, a dropping funnel and a blowing tube was prepared, 36.3 g (0.88 moles) of 97% sodium hydroxide and 43.3 g of water were introduced thereto, and the resultant was stirred until it became uniform. 2.8 g (composition ratio: 15.7% by weight of β-mercaptopropionic acid, 81.5% by weight of thiodipropionic acid and 2.3% by weight of dithiodipropionic acid) of distillation residue (A) in a state with fluidity was slowly added to the sodium hydroxide aqueous solution while keeping the temperature at the range of 90° C. to 95° C. While maintaining the inner temperature at the range of 45° C. to 50° C., 12.24 g (0.17 moles) of acrylic acid was added dropwise from the dropping funnel over 0.5 hours.

After the dropping ended, 12.6 g (0.37 moles) of hydrogen sulfide gas was blown into the reaction solution through the flow meter from a liquefied hydrogen sulfide bombe (manufactured by Sumitomo Seika Chemicals Co., Ltd.) at the same temperature over 90 minutes. After the blowing ended, the temperature was raised to 100° C., and reaction was performed at the same temperature over 8 hours.

After the reaction ended, when quantitative analysis of the reaction solution was performed by a HPLC, 0.172 mol % of β-mercapto propionic acid sodium salt, and 0.013 mol % of thiodipropionic acid sodium salt and 0.0006 mol % of dithiodipropionic acid sodium salt as a by-product were produced.

Neutralization, extraction and distillation operation were performed in the same manner as Example 1, and 17.5 g (0.165 moles) of β-mercaptopropionic acid having a purity of 99.9% was obtained as a main fraction (Reaction 2). The yield of β-mercaptopropionic acid was 89.2% with respect to acrylic acid (14.4 g+12.2 g) used in the first reaction and the first reaction of distillation residue recycling.

In addition, 2.9 g (15.3% by weight (0.004 moles) of β-mercaptopropionic acid, 79.3% by weight (0.013 moles) of thiodipropionic acid, and 4.4% by weight (0.0006 moles) of dithiodipropionic acid) as a residue (distillation residue (B)) of distillation kettle were obtained.

The raw materials supplied to a reaction in Example 5, and compositions of the obtained reaction product are described in Table 1.

TABLE 1

| | Reaction | | | | Reaction product | | | | | |
|---|---|---|---|---|---|---|---|---|---|---|
| | | | | | β-mercaptopropionic acid | | Composition of distillation residue | | | |
| Reaction No. | NaOH (mol) | Acrylic acid (mol) | $H_2S$ (mol) | Distillation residue No. | Production amount (mol) | Cumulative yield * (%) | No | β-mercaptopropionic acid (mol) | Thiodipropionic acid (mol) | Dithiodipropionic acid (mol) |
| 1 | 0.88 | 0.20 | 0.37 | — | 0.165 | 82.5 | A | 0.004 | 0.013 | 0.0003 |
| 2 | 0.88 | 0.17 | 0.37 | A | 0.165 | 89.2 | B | 0.004 | 0.013 | 0.0006 |

* (cumulative production amount (mol) of β-mercaptopropionic acid/cumulative used amount (mol) of acrylic acid) × 100

Example 6

Reaction was performed in the same manner as Example 1 (Reaction 1). Then, using the distillation residue (A) obtained in Reaction 1, a reaction was performed under the same conditions as Example 4 and the amounts of raw materials supplied to a reaction were changed as described in Table 2 (Reaction 2). In the same manner, using the distillation residue obtained in the previous reaction, a reaction was performed under the same conditions as Example 4 and the amounts of raw materials supplied to a reaction was changed as described in Table 2 at four times (Reactions 3 to 6).

In this manner, by using the obtained distillation residue in a next reaction, a recycling was performed at five times. As a result, the yield of β-mercaptopropionic acid (purity 99.9%) obtained as a distillation main fraction was 94.4% with respect to acrylic acid used for performing the first reaction (Reaction 1) and the first to fifth recycling (Reactions 2 to 6).

The raw materials supplied to a reaction in Example 6, and compositions of the obtained reaction product are described in Table 2.

TABLE 2

| | | Reaction | | | Reaction product | | | | | |
|---|---|---|---|---|---|---|---|---|---|---|
| | | | | | β-mercaptopropionic acid | | Composition of distillation residue | | | |
| Reaction No. | NaOH (mol) | Acrylic acid (mol) | $H_2S$ (mol) | Distillation residue No. | Production amount (mol) | Cumulative yield * (%) | No | β-mercaptopropionic acid (mol) | Thiodipropionic acid (mol) | Dithiodipropionic acid (mol) |
| 1 | 0.88 | 0.20 | 0.37 | — | 0.165 | 82.5 | A | 0.004 | 0.013 | 0.0003 |
| 2 | 0.88 | 0.17 | 0.37 | A | 0.165 | 89.2 | B | 0.004 | 0.013 | 0.0006 |
| 3 | 0.88 | 0.17 | 0.37 | B | 0.165 | 91.7 | C | 0.004 | 0.013 | 0.0009 |
| 4 | 0.88 | 0.17 | 0.37 | C | 0.165 | 93.0 | D | 0.004 | 0.013 | 0.0012 |
| 5 | 0.88 | 0.17 | 0.37 | D | 0.165 | 93.8 | E | 0.004 | 0.013 | 0.0015 |
| 6 | 0.88 | 0.17 | 0.37 | E | 0.165 | 94.4 | F | 0.004 | 0.013 | 0.0018 |

* (cumulative production amount (mol) of β-mercaptopropionic acid/cumulative used amount (mol) of acrylic acid) × 100

Comparative Example 1

A 5-necked flask provided with a stirring apparatus, a thermometer, a cooling tube, a dropping funnel and a blowing tube was prepared, 21.0 g (0.51 moles) of 97% sodium hydroxide and 41.6 g of water were introduced thereto, 29.6 g (0.37 moles) of 70% sodium hydrosulfide (manufactured by Wako Pure Chemical Industries, Ltd.) was further introduced thereto, and the resultant was stirred until it became uniform.

While maintaining the inner temperature of the flask at the range of 45° C. to 50° C. by heating the flask in an oil bath, 14.4 g (0.20 moles) of acrylic acid was added dropwise from the dropping funnel over about 0.5 hours. After the dropping ended, the temperature was raised to 100° C., and reaction was performed at the same temperature over 8 hours.

After the reaction ended, when analysis of the reaction mass was performed by a HPLC, 87.3 mol % of β-mercaptopropionic acid sodium salt, and 12.0 mol % of thiodipropionic acid sodium salt and 0.7 mol % of dithiodipropionic acid sodium salt as a by-product were produced.

While bubbling nitrogen gas into the reaction system, 129.5 g (0.462 moles) of 35% aqueous sulfuric acid was added dropwise over 2.5 hours to neutralize the reaction solution. Hydrogen sulfide generated at this time was discharged from the upper portion of the condenser out of the system. In addition, in the reaction mass composition after the neutralization, β-mercaptopropionic acid was 79.3 mol %. As a by-product, thiodipropionic acid was 12.0 mol % and dithiodipropionic acid was increased to 8.7 mol %.

After the degassing ended, the operations in the same manner as Example 1 were performed in the same manner as Example 1, and 16.2 g (0.152 moles) of β-mercaptopropionic acid having a purity of 99.9% was obtained as a main fraction. The yield with respect to acrylic acid was 76.1%.

Comparative Example 2

A 5-necked flask provided with a stirring apparatus, a thermometer, a cooling tube, a dropping funnel and a blowing tube was prepared, 20.6 g (0.50 moles) of 97% sodium hydroxide and 43.3 g of water were introduced thereto, and the resultant was stirred until it became uniform.

While maintaining the inner temperature of the flask at the range of 45° C. to 50° C. by heating the flask in an oil bath, 14.4 g (0.20 moles) of acrylic acid was added dropwise from the dropping funnel over about 0.5 hours.

After the dropping ended, 12.6 g (0.37 moles) of hydrogen sulfide gas was blown into the reaction solution through the flow meter from a liquefied hydrogen sulfide bombe (manufactured by Sumitomo Seika Chemicals Co., Ltd.) at the same temperature over 88 minutes. After the blowing ended, the temperature was raised to 100° C., and reaction was performed at the same temperature over 8 hours.

After the reaction ended, when quantitative analysis of the reaction mass was performed by a HPLC, 49.3 mol % of β-mercaptopropionic acid sodium salt, and 48.8 mol % of thiodipropionic acid sodium salt and 1.3 mol % of dithiodipropionic acid sodium salt as a by-product were produced.

The results of Examples 1 to 4 and Comparative Examples 1 and 2 are summarized and described in Table 3.

TABLE 3

| | Moles of used compound | | | | | Addition reaction achievement (mol %/AA) | | | Reaction achievement after neutralization (mol %/AA) | | |
|---|---|---|---|---|---|---|---|---|---|---|---|
| | Acrylic acid | $H_2S$ | | | | | | | | | |
| | (a) | (b) | a + b | NaOH | NaSH | β-MPA | S | SS | β-MPA | S | SS |
| Example 1 | 0.2 | 0.37 | 0.57 | 0.88 | — | 86.0 | 13.0 | 0.4 | 86.0 | 13.0 | 0.3 |
| Example 2 | 0.2 | 0.37 | 0.57 | 0.88 | — | 86.1 | 12.9 | 0.4 | 86.5 | 12.9 | 0.0 |
| Example 3 | 0.2 | 0.37 | 0.57 | 0.88 | — | 87.4 | 11.8 | 0.8 | — | — | — |
| Example 4 | 0.2 | 0.52 | 0.72 | 1.14 | — | 94.8 | 4.6 | 0.2 | — | — | — |
| Comparative Example 1 | 0.2 | — | — | 0.51 | 0.37 | 87.3 | 12 | 0.7 | 79.3 | 12.0 | 8.7 |

TABLE 3-continued

| | Moles of used compound | | | | | Addition reaction achievement (mol %/AA) | | | Reaction achievement after neutralization (mol %/AA) | | |
|---|---|---|---|---|---|---|---|---|---|---|---|
| | Acrylic acid (a) | $H_2S$ (b) | a + b | NaOH | NaSH | β-MPA | S | SS | β-MPA | S | SS |
| Comparative Example 2 | 0.2 | 0.37 | 0.57 | 0.5 | — | 49.3 | 48.8 | 1.3 | — | — | — |

AA: acrylic acid
β-MPA: β-mercaptopropionic acid sodium salt
S: thiodipropionic acid sodium salt
SS: dithiodipropionic acid sodium salt
AA: acrylic acid
β-MPA: β-mercaptopropionic acid sodium salt
S: thiodipropionic acid sodium salt
SS: dithiodipropionic acid sodium salt The present application claims priority based on Japanese Patent Application no. 2011-253453, filed on Nov. 21, 2011, the content of which is incorporated herein by reference.

The invention claimed is:

1. A process for preparing β-mercaptocarboxylic acid represented by the following General Formula (3), comprising:
reacting hydrogen sulfide, alkali hydroxide represented by a formula: XOH (X represents Na or K), and unsaturated carboxylic acid represented by the following General Formula (1) under atmospheric pressure to obtain a reaction solution including a compound represented by the following General Formula (2); and
neutralizing the reaction solution in an acid,
wherein an amount of the alkali hydroxide is equal to or greater than total moles of the unsaturated carboxylic acid and the hydrogen sulfide,

(1)

wherein, in Formula (1), each of $R^1$ and $R^2$ independently represents hydrogen or an alkyl group of C1 to C4, and may be the same as or different from each other,

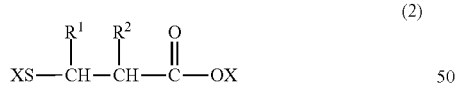
(2)

wherein, in Formula (2), $R^1$ and $R^2$ have the same definition as in Formula (1), X has the same definition as in alkali hydroxide represented by a formula: XOH, and

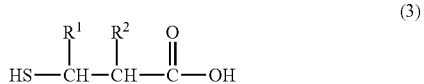
(3)

wherein, in Formula (3), $R^1$ and $R^2$ have the same definition as in Formula (1).

2. The process for preparing β-mercaptocarboxylic acid according to claim 1,
wherein the step for obtaining the reaction solution is performed in the presence of sulfur atom.

3. The process for preparing β-mercaptocarboxylic acid according to claim 1,
wherein the step of neutralizing the reaction solution in an acid includes a step in which dithiodicarboxylic acid produced from β-mercaptocarboxylic acid is reduced by a metal which is at least one selected from the group consisting of zinc, iron and tin to obtain β-mercaptocarboxylic acid.

4. The process for preparing β-mercaptocarboxylic acid according to claim 2,
wherein the step of neutralizing the reaction solution in an acid includes a step in which dithiodicarboxylic acid produced from β-mercaptocarboxylic acid is reduced by a metal which is at least one selected from the group consisting of zinc, iron and tin to obtain β-mercaptocarboxylic acid.

* * * * *